(12) United States Patent
Abood

(10) Patent No.: US 11,596,193 B1
(45) Date of Patent: *Mar. 7, 2023

(54) CARE GIVER DISPLAY SURGICAL CAP TO CONTROL PATIENT BODY TEMPERATURE

(71) Applicant: Equalizer Technology, LLC, Rocky River, OH (US)

(72) Inventor: David G. Abood, Rocky River, OH (US)

(73) Assignee: EQUALIZER TECHNOLOGY LLC, Rocky River, OH (US)

(*) Notice: Subject to any disclaimer, the term of this patent is extended or adjusted under 35 U.S.C. 154(b) by 936 days.

This patent is subject to a terminal disclaimer.

(21) Appl. No.: 16/242,305

(22) Filed: Jan. 8, 2019

Related U.S. Application Data

(63) Continuation-in-part of application No. 14/850,950, filed on Sep. 10, 2015, now abandoned, which is a continuation-in-part of application No. 13/692,060, filed on Dec. 3, 2012, which is a continuation-in-part of application No. 12/649,887, filed on Dec. 30, 2009, now Pat. No. 10,219,568.

(60) Provisional application No. 62/617,715, filed on Jan. 16, 2018.

(51) Int. Cl.
```
A42B 1/04        (2021.01)
A42B 1/242       (2021.01)
A42B 1/008       (2021.01)
A42B 1/045       (2021.01)
A61B 5/01        (2006.01)
A61B 5/00        (2006.01)
A61F 7/02        (2006.01)
A42B 1/0186      (2021.01)
A61F 7/00        (2006.01)
```

(52) U.S. Cl.
CPC .............. *A42B 1/242* (2013.01); *A42B 1/008* (2013.01); *A42B 1/0186* (2021.01); *A42B 1/045* (2013.01); *A61B 5/01* (2013.01); *A61B 5/7445* (2013.01); *A61F 7/02* (2013.01); *A61B 2505/05* (2013.01); *A61F 2007/0005* (2013.01); *A61F 2007/0008* (2013.01); *A61F 2007/0228* (2013.01); *A61F 2007/0233* (2013.01); *A61F 2007/0266* (2013.01); *A61F 2007/0288* (2013.01)

(58) Field of Classification Search
CPC ....... A42B 1/242; A42B 1/0186; A42B 1/008; A42B 1/045; A61B 5/01; A61B 5/7445
See application file for complete search history.

(56) References Cited

U.S. PATENT DOCUMENTS 1,589,614 A * 6/1926 Peters .................... A42B 1/041
                                                     D2/881
2,644,949 A * 7/1953 Greenberg ........... A42B 1/0189
                                                     2/172

(Continued)

*Primary Examiner* — Richale L Quinn
(74) *Attorney, Agent, or Firm* — Gugliotta & Gugliotta, LPA

(57) ABSTRACT

The present invention relates generally to a device and a method that maintains a patient's body temperature during surgical exposure and, more specifically, to a surgical, insulative cap that forms a viewing window and is used in conjunction with a medical temperature trend indicator. The cap is contoured to the patient's head. The instant abstract is neither intended to define the invention disclosed in this specification nor intended to limit the scope of the invention in any way.

14 Claims, 5 Drawing Sheets

(56) References Cited

U.S. PATENT DOCUMENTS

| | | | | |
|---|---|---|---|---|
| 2,726,398 A * | 12/1955 | Cooper | A42B 1/12 | 2/174 |
| 2,874,387 A * | 2/1959 | Bannister | A42B 1/0182 | 2/10 |
| 3,296,582 A * | 1/1967 | Ide | G10K 11/002 | 181/175 |
| 3,321,774 A * | 5/1967 | Tames | A42B 1/012 | 2/181 |
| 3,512,181 A * | 5/1970 | Osborne | A42B 1/012 | D2/881 |
| 4,061,898 A * | 12/1977 | Murray | A42B 1/008 | 219/549 |
| 4,552,149 A * | 11/1985 | Tatsuki | A61F 7/10 | 607/110 |
| 4,615,754 A * | 10/1986 | Waugh | B60R 13/005 | 156/247 |
| 5,146,630 A * | 9/1992 | Richard | A41D 20/005 | 2/171.2 |
| 5,181,277 A * | 1/1993 | Sherman | A42C 5/02 | 2/209.12 |
| 5,197,292 A * | 3/1993 | McPherson | A42B 1/008 | 62/530 |
| 5,302,806 A * | 4/1994 | Simmons | A42B 3/285 | 607/108 |
| 5,365,607 A * | 11/1994 | Benevento, Jr. | A42B 1/008 | 2/171.1 |
| 5,480,688 A * | 1/1996 | Kaumeyer | B60R 13/04 | 52/716.5 |
| 5,496,357 A * | 3/1996 | Jensen | A61F 7/0097 | 607/108 |
| 5,557,807 A * | 9/1996 | Hujar | A42B 1/0187 | 2/209.13 |
| 5,603,728 A * | 2/1997 | Pachys | A61F 7/02 | 607/104 |
| 5,605,144 A * | 2/1997 | Simmons | A42B 3/10 | 2/171.2 |
| 5,630,230 A * | 5/1997 | Fujino | A42B 3/10 | 2/200.1 |
| 5,850,636 A * | 12/1998 | Reuven | A42B 1/008 | 2/200.1 |
| 6,014,776 A * | 1/2000 | DeVinzio | A42B 1/041 | 2/172 |
| 6,397,399 B1 * | 6/2002 | Lampe | A63B 71/10 | 2/171.2 |
| 6,557,179 B1 * | 5/2003 | Reuven | A42B 1/008 | 2/209 |
| 6,817,039 B1 * | 11/2004 | Grilliot | A42B 3/14 | 2/416 |
| 6,918,138 B2 * | 7/2005 | Donovan | A45D 19/14 | 2/204 |
| 7,028,344 B2 * | 4/2006 | Toth | A42B 3/122 | 2/171.2 |
| 7,043,761 B2 * | 5/2006 | Epling | A42C 5/04 | 2/200.1 |
| 8,226,698 B2 * | 7/2012 | Edelman | A61F 7/02 | 607/104 |
| 8,262,601 B2 * | 9/2012 | Cumming | A61F 13/12 | 602/14 |
| 8,533,869 B1 * | 9/2013 | Capuano | A42B 3/124 | 2/411 |
| 8,613,114 B1 * | 12/2013 | Olivares Velasco | A41D 31/065 | 2/171.1 |
| 8,781,548 B2 * | 7/2014 | Besko | A61B 5/6806 | 600/324 |
| 8,819,867 B1 * | 9/2014 | Boada | A42B 1/24 | 2/171.2 |
| D714,666 S * | 10/2014 | Abood | D10/57 | |
| 9,095,183 B2 * | 8/2015 | Aronson | A42B 1/0182 | |
| 9,149,393 B2 * | 10/2015 | Cumming | A61F 13/12 | |
| 9,578,914 B2 * | 2/2017 | Fierro | A63B 33/00 | |
| 9,907,346 B2 * | 3/2018 | Hanson | A42B 3/069 | |
| 10,080,394 B2 * | 9/2018 | Johnston | A41D 20/00 | |
| 10,085,495 B2 * | 10/2018 | Kitaura | A41D 13/005 | |
| 10,219,568 B1 * | 3/2019 | Saluan | A42B 1/012 | |
| 10,226,206 B2 * | 3/2019 | Esenaliev | A61B 5/14553 | |
| 10,265,019 B2 * | 4/2019 | Gertsch | A61B 5/0008 | |
| 10,383,386 B2 * | 8/2019 | Abraham | B32B 25/20 | |
| D876,970 S * | 3/2020 | Duck | D10/57 | |
| 10,624,403 B2 * | 4/2020 | Seela | A42B 1/24 | |
| 2002/0002730 A1 * | 1/2002 | Dennis | A42B 3/127 | 2/414 |
| 2002/0100106 A1 * | 8/2002 | Simmons | A42C 5/04 | 2/171.2 |
| 2003/0200598 A1 * | 10/2003 | Jessie | A42B 3/122 | 2/413 |
| 2003/0221241 A1 * | 12/2003 | Rivera | A41D 20/005 | 2/170 |
| 2003/0233697 A1 * | 12/2003 | Tsai | A41D 13/0053 | 2/209.13 |
| 2004/0040066 A1 * | 3/2004 | Hardenbrook | A45D 19/18 | 2/171 |
| 2004/0226077 A1 * | 11/2004 | Toth | A42B 3/127 | 2/422 |
| 2004/0244096 A1 * | 12/2004 | Claro | A42B 1/22 | 2/195.2 |
| 2005/0060911 A1 * | 3/2005 | Falone | A63B 71/12 | 36/44 |
| 2005/0183182 A1 * | 8/2005 | Keenan | A61B 90/04 | 2/114 |
| 2005/0268382 A1 * | 12/2005 | Epling | A42B 1/0189 | 2/411 |
| 2006/0079794 A1 * | 4/2006 | Liu | A61B 5/6806 | 600/502 |
| 2006/0100530 A1 * | 5/2006 | Kliot | A61B 5/681 | 600/483 |
| 2007/0157358 A1 * | 7/2007 | Sharon | G09F 3/02 | 2/69 |
| 2008/0146958 A1 * | 6/2008 | Guillory | A61B 5/4094 | 600/544 |
| 2009/0069652 A1 * | 3/2009 | Lee | A61B 5/14552 | 600/323 |
| 2010/0076337 A1 * | 3/2010 | Medina | A61B 5/6804 | 2/171.2 |
| 2010/0081904 A1 * | 4/2010 | Medina | A61B 5/14552 | 600/323 |
| 2010/0107307 A1 * | 5/2010 | Lee | A42C 5/02 | 2/181 |
| 2010/0132094 A1 * | 6/2010 | Mullen | A42C 5/02 | 2/209.13 |
| 2010/0138980 A1 * | 6/2010 | Duda | A42C 5/02 | 2/184 |
| 2010/0249554 A1 * | 9/2010 | McKenna | A61B 5/14552 | 600/324 |
| 2010/0249557 A1 * | 9/2010 | Besko | A61B 5/6814 | 600/340 |
| 2011/0094012 A1 * | 4/2011 | Toth | A42B 3/121 | 62/530 |
| 2014/0026284 A1 * | 1/2014 | Yates | A63B 33/00 | 2/67 |
| 2014/0173806 A1 * | 6/2014 | Fournier | A41D 20/00 | 2/170 |
| 2014/0338099 A1 * | 11/2014 | Marscellas | A42B 1/012 | 2/209.13 |
| 2014/0379058 A1 * | 12/2014 | Farrago | A61F 7/02 | 607/110 |
| 2016/0021962 A1 * | 1/2016 | Lacy | A42B 1/22 | 2/181 |
| 2016/0037625 A1 * | 2/2016 | Huitema | H05K 5/0017 | 361/749 |
| 2016/0058084 A1 * | 3/2016 | Stevenson | A41D 20/005 | 2/209.13 |
| 2017/0065872 A1 * | 3/2017 | Kelley | H04W 4/80 | |
| 2017/0224530 A1 * | 8/2017 | Farrago | A61F 7/02 | |
| 2019/0209381 A9 * | 7/2019 | Cumming | A61F 13/00059 | |
| 2021/0217842 A1 * | 7/2021 | Park | G09G 3/2003 | |
| 2021/0244573 A1 * | 8/2021 | Kastros | A61F 13/00046 | |

\* cited by examiner

CARE GIVER DISPLAY SURGICAL CAP TO CONTROL PATIENT BODY TEMPERATURE

RELATED APPLICATIONS

The present application claims benefit of U.S. Provisional Application 62/617,715, and is a Continuation in Part of U.S. Ser. No. 12/649,887 filed on Dec. 30, 2009, both incorporated by reference herein as if fully rewritten.

BACKGROUND OF THE INVENTION

1. Field of the Invention

The present invention relates generally to a device and a method that maintains a patient's body temperature during surgical exposure and, more specifically, to a surgical, insulative cap that is contoured to the patient's head.

2. Description of the Related Art

The vast majority of patients that undergo anesthetic experience some level of hypothermia. The decrease in temperature is variable, but it worsens in the procedures that involve larger and lengthier surgical exposures. The state of relative hypothermia can significantly and adversely affect a patient, especially during the perioperative and the postoperative periods. However, due to physical and logistical limitations, it is difficult to continuously monitor a surgical patient's body temperature at most times from perioperative, operative, and postoperative periods. One solution has been the development of devices called 'trend monitors'. A trend monitor is a noninvasive skin mounted device, usually of a thin plastic film, that it placed in direct physical communication with the patient's skin (usually on the patient's forehead, arm or chest). The film includes a color changing element that forms a scale that indicates temperature information noninvasively for consistent thermoregulation monitoring of patients. Temperature trend indicators can be adjusted to core-body temperature, or other temperature metrics to ensure a most accurate measurement in a number of care settings. Such devices can provide continuous, accurate temperature trending noninvasively sufficiently to detect malignant hyperthermia or hypothermia. Complications related to hypothermia include myocardia ischemia, hypertension, tachycardia, and the infections that lead to unanticipated mortality and morbidity. Because most of a patient's heat capacity is lost through an uncovered head, the medical industry is now continuously monitoring data to indicate the problem, but has not yet found a solution to combating the problem by developing a means to keep the patient euthermic.

The present invention teaches a surgical, insulative cap that is designed both to contour a patient's head and ears and to maintain its position during surgery in combination with a temperature trend indicator that can provide continuous, accurate temperature trending indicator sufficient to detect malignant hyperthermia or hypothermia.

SUMMARY OF THE INVENTION

It is an object of the present invention to provide a flexible and a disposable surgical cap that is worn by patients during surgical procedures.

It is an object of the present invention to reduce the risks to patients, especially to the elderly patients at higher risks, for developing hypertension, tachycardia and the other conditions related to surgical hypothermia.

It is an object that the present cap is comprised of an insulative material that is both stretchable and flexible to provide a means for the cap to follow the contour of a head.

It is an object that the present surgical cap is constructed to minimize exposures to fibrous materials and, as such, to remove any habitat for bacterial growth.

It is an object of the present invention to provide such a surgical cap that incorporates the functions use, in combination, of a medical temperature trend indicator.

It is envisioned that the present surgical cap includes an insulative inner portion and a shell fabricated from the materials sold under the trademarks THERMALITE®, THINSULATE® or OUTLAST®. More specifically, the cap includes a ceramic fiber material, a commercially synthetic material having fibers that contain a plurality of microencapsulated and paraffinic hydrocarbons (hereinafter a "phase change material") and a synthetic microfiber having a composition approximating 65% olefin and 35% polyester. The cap extends over a greater portion of a patient's forehead, over the patient's ears and behind the head to reach as far as the top of the lumbar spine.

It is an object of the present cap to prevent excessive airflow between the cap material and a patient's head by eliminating the large air gap between the two. This object is accomplished by minimizing the amount of surface area covered by the cap while also retaining the cap on the patient's head.

It is envisioned that a reflective material may be incorporated into the disclosed invention. Reflective materials may be added to the fibrous insulative materials.

It is an object of the present invention to provide a means to adjust the surgical cap to further ensure a close-fit.

It is an object that such means includes gusseted portions with an attachment mechanism selected from the group comprising VELCRO™ or a chemical adhesive having a peel-away protective cover.

It is an object of the present invention to provide a chin strap as a means to ensure the grip of the surgical cap to the head. It is envisioned that the chin strap is attached to the lower right and the lower left aspects of the surgical cap.

It is an object of the present invention to provide a clear rubberized or elastomeric type material to form a viewing window located at the forehead region to accommodate a medical temperature trend indicator. It is envisioned that the window will be flat on the inside, providing an urging force to maintain direct physical contact of the temperature trend indicator to the patient's skin.

The present invention will maintain its position during and after the repeated times an anesthesiologist manipulates the head's position to access monitor apparatuses.

The present invention continues to provide access to the central venous region.

The present invention will provide the proper position and contact of the temperature trend indicator for optimal use, while at the same time allowing for indirect viewing positions.

The present invention may similarly be used for nonsurgical patients with temperature regulatory issues, such as immunocompromised individuals and cancer patients.

It is a final object of the present invention to provide all of the advantages that the foregoing objects entail. The present invention departs from the current designs to overcome their respective disadvantages.

BRIEF DESCRIPTION OF THE DRAWINGS

The advantages and the features of the present invention will become better understood with reference to the following more detailed description and the claims taken in conjunction with the accompanying drawings, in which like elements are identified with like symbols, and in which:

DESCRIPTION OF THE PREFERRED EMBODIMENTS

Figure 1:
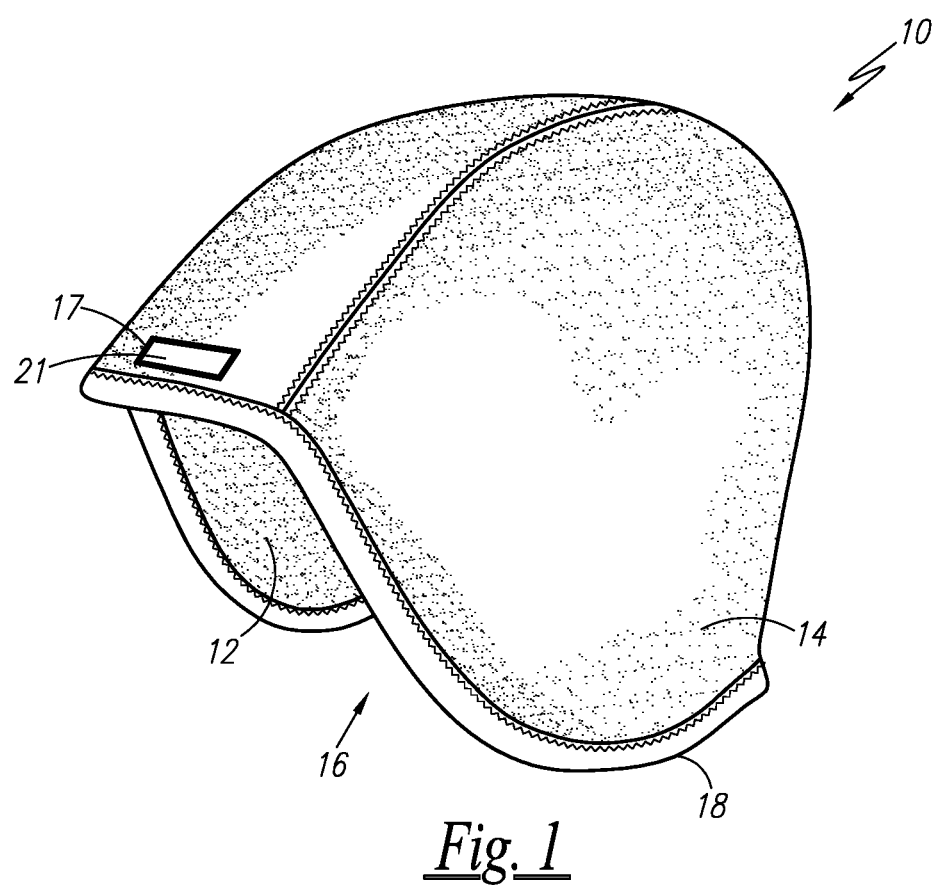
FIG. 1 is a perspective view of a Surgical Cap to Control Patient Body Temperature according to a preferred embodiment of the present invention.

The best mode for carrying out the invention is presented in terms of its preferred embodiment, herein depicted within the FIGS. 1-7.

1. Detailed Description of the Figures

Referring now to FIG. 1-5, a covering unit, generally noted as 10, is shown for covering a patient's head for maintaining the head temperature and core body temperature within euthermic range during surgery. The covering unit 10 covers a substantial portion of the head 70, as will be described in greater detail below and forms a multi-part shell component having an inner surface 12 adapted for closely fitting the contours of a patient's head so as to prevent open air space between the head and an inner surface. The shell component further has an outer surface 14, and forming an opening 16 circumscribed by a gripping lower edge 18. This gripping lower edge 18 forms a gripping means for gripping to a patient's head in a manner such as to impede said the head covering unit from coming off of the patient's head during surgery.

Near the lower edge 18 at the forehead region of the surface is formed a viewing window 19. In its preferred embodiment the viewing window is formed of a clear rubberized or elastomeric type material creating a lense like structure that is flat on the inside 17a, and slightly convex on the outside 17b. The gripping means, in combination with the flat inside surface 17a, providing an urging force to maintain direct physical contact of a temperature trend indicator 21 to the patient's skin. The convex outer surface 17b forms lense-like viewing window that provides better viewing of the surface indicia of the temperature trend indicator 21 over a wider range of viewing angles. The temperature trend indicator 21 is anticipated as being a liquid crystal temperature indicator that provides a visual indicia that corresponds with the patient's core body temperature within an euthermic range. While various types of temperature trend indicators are currently in use, and it would be obvious to one skilled in the relevant art, in light of the present disclosure, that the specific type of temperature trend indicator being used should not form a limitation on the overall functions and features of the present invention, for the purpose of disclosing the enablement of the preferred embodiment of the present invention, the use of a Crystalline® II type liquid crystal indicator as commercially available form Sharn, Inc. of Tamp, Fla. is anticipated as used with the current invention. Such a selection, while generally a design choice, has shown to provide preferred functionality in that it forms a planar, flexible member that adheres to the inside surface 17a for continuous viewing, incorporates adhesive on a rear side to maintain continuous thermal contact with the patient's skin in a manner that is maintained even when the covering unit 10 is removed, and provides visually discernible patient temperature indicia correlated to the preferred patient core body temperature euthermic range.

Figure 6:
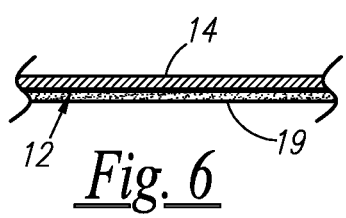
FIG. 6 is a partial cross sectional view taken along lines VI-VI of FIG. 4.
Figure 7:
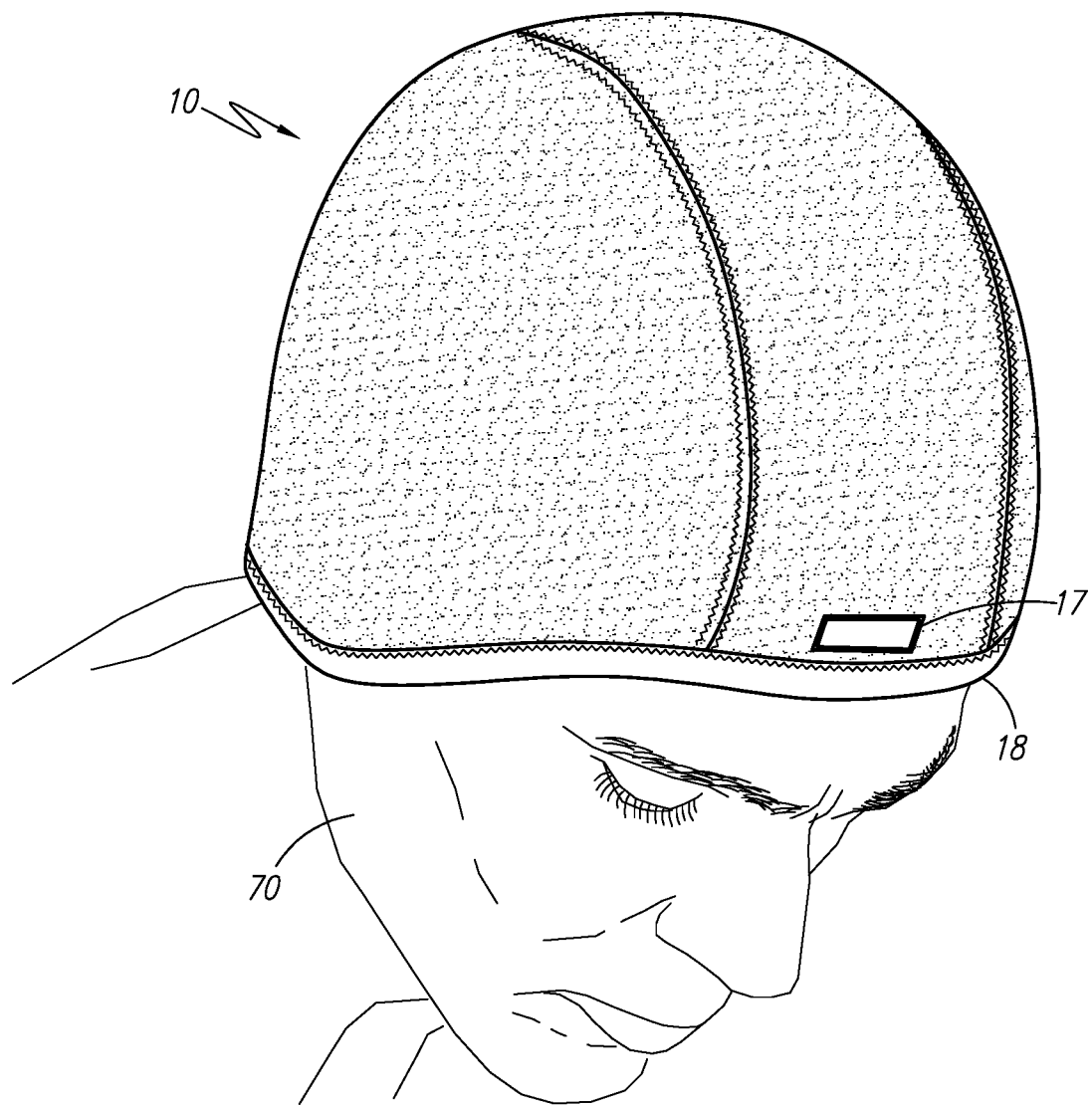
FIG. 7 is a perspective view of a surgical sap to control patient body temperature according to a preferred embodiment of the present invention, wherein the surgical cap is shown in cooperation with a wearer's head; and, FIG. 8 is a perspective view of a surgical cap to control patient body temperature according to an alternate embodiment of the present invention.

The shell component 14 preferably will provide insulating properties, and may include an insulating filling. However, in greater detail as shown in FIG. 6, the material of the shell component is anticipated as being thicker than 1 mm and less than 2 mm thick and adapted for positioning over both lateral side portions of the head. This shell is of a thickness suitable for maintaining the patient's head temperature within euthermic range.

Figure 5:
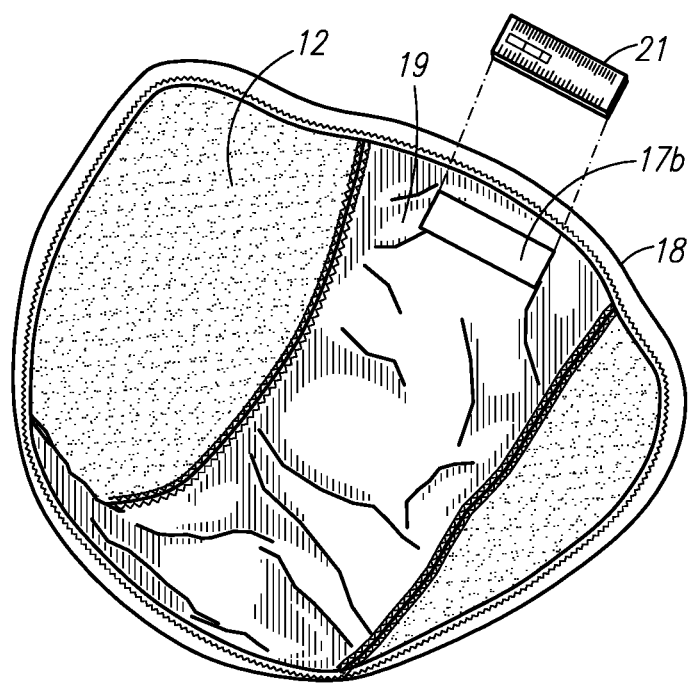
FIG. 5 is a reverse perspective showing the inner portion thereof.

As additionally anticipated and shown best in conjunction with FIG. 5-6, an additional insulating component 19 lining a portion of the inner surface 12.

Also illustrated in FIG. 1-7, the cap 10 will preferably cover below the mid point of the external auditory meatus bilaterally in addition to the rear portion of the head and upper neck region. The material covering the head has been designed to be in contact with the head in all covered areas so as to prevent a signification amount of air space between the head and the inner material covering the head. To accomplish this, the shell component is made from a pattern cut that is asymmetric from a section of the covering unit adapted for covering the front of the head and a section of the covering unit adapted for covering the rear of the head covering unit, such that the pattern cut has a concave pattern so as to emulate the shape of the front and rear of the head to prohibit the head covering unit from coming off of the head during surgery.

It is preferred that the shell component comprise insulative properties. The shell component may further include an insulative filling.

It is anticipated that the material of the shell component, as shown in FIG. 6, approximates a thickness no less than 1-mm and preferably between 1-mm and 2-mm or greater. The shell's thickness is not limited to the approximations disclosed herein, but may alternatively comprise any thickness that both maintains euthermic range and adapts to a position over both lateral portions of the patient's head.

It is additionally anticipated that an additional insulative component 19 lines a portion of the inner surface 12, as best shown in FIGS. 5 and 6. The insulative component 19 comprises material having a thickness greater than 2-mm at the areas adapted to cover the posterior, the anterior and the top portions of the head. The insulative component 19 comprises material having a thickness less than 2-mm at the areas adapted to cover both of the lateral portions.

The surgical cover 10 insulates a greater portion of the patient's head along approximately the central third, the anterior and the posterior portions.

As also illustrated in FIGS. 1-7, the surgical cap 10 preferably covers below the midpoint of the external auditory meatus bilaterally in addition to the rear portion of the head and the upper neck region. The inner material that covers the head is designed to be in direct contact with the head to prevent the adverse effects a surgical cap having air gaps has on patient hypothermia. The direct contact is accomplished by means of a shell component made from a pattern cut asymmetrically from a section of the covering unit adapted to cover the front of the head and from a section of the covering unit adapted to cover the rear of the head. The pattern cut is concave to emulate the shape of the front and the rear of a head; it prohibits the surgical cap 10 from falling off during surgery. The pattern forms a gap less than ¾ inch, preferably less than ½ inch and most preferably less than ¼ inch.

It is additionally contemplated that the surgical cap 10 include material that comprises a temperature regulating microfiber. The enclosed cap may further incorporate a chin strap attached to the lower right and the lower left aspects of the surgical cover 10.

It is envisioned that the cap 10 is manufactured in various sizes, e.g., the standard sizes that include extra-small, small, medium, large, extra-large and the like. For a more efficient fit, the surgical cap 10 may comprise the various standard sizes for different age ranges. Additionally, an adjustment or a take-up mechanism may be used to ensure a close-fit over the patient's head without pressing on the patient's head. The surgical cap 10 laterally grips below the patient's external auditory meatus. Finally, it is envisioned that the material used in the head covering unit does not emit sparks nor is it static conductive. It may even be made of a fire retardant material.

Figure 2:
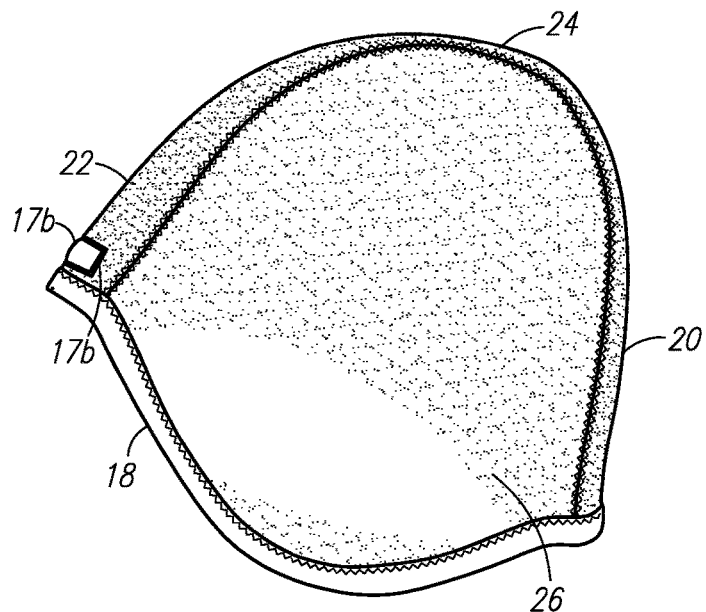
FIG. 2 is a side elevational view thereof.
Figure 3:
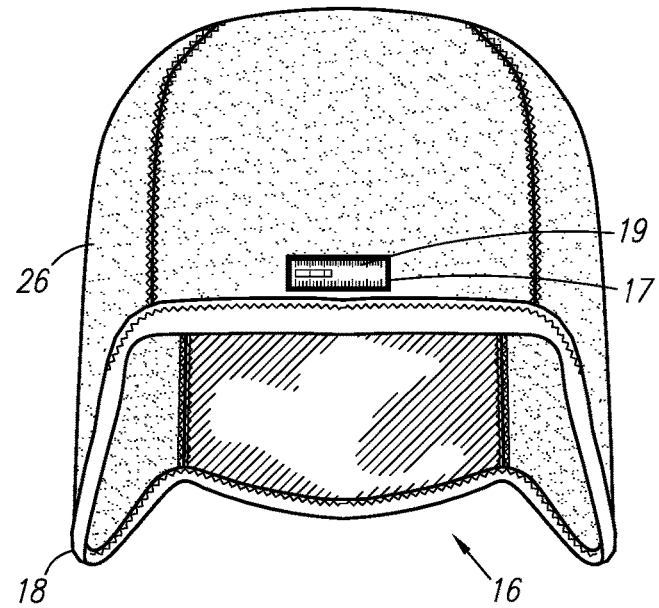
FIG. 3 is a front elevational view thereof.
Figure 4:
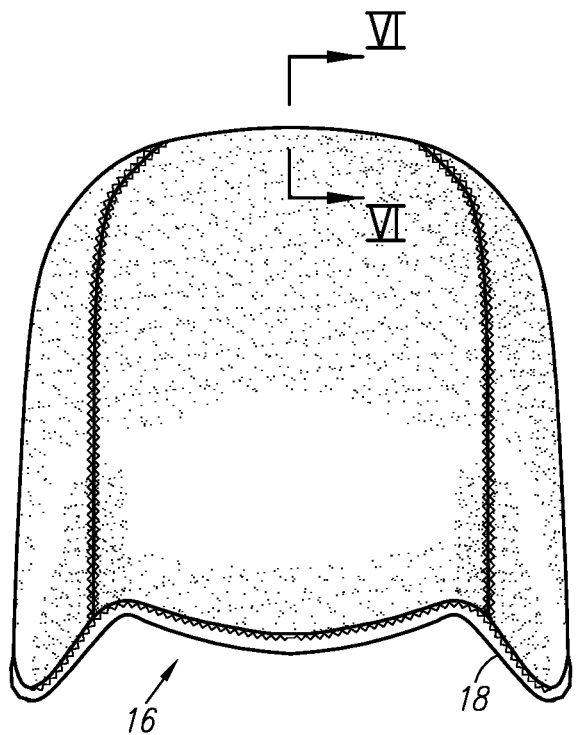
FIG. 4 is a rear elevational view thereof.

FIGS. 1-3 further illustrate that an embodiment of the disclosed invention can be made from a pattern cut asymmetrically from a section of the surgical cap 10 adapted to cover the front of the head and a section of the surgical cap 10 adapted to cover the rear of the head. Such a pattern is concave to emulate the shape of the front and the rear of the head and to prohibit the head covering unit from falling off during surgery. This embodiment includes a rear panel 20, a front panel 22, a top panel 24, and a medial and a lateral side panel 26 covering the mid point of the external auditory meatus bilaterally. The seams between the sides contain the external aspects to prevent the surgical cap 10 from moving when it is laid on the posterior side, the medial or lateral side of the body.

FIGS. 1-3 further illustrated that an example of the disclosed invention can be made from a pattern cut that is asymmetric from a section of the covering unit adapted for covering the front of the head and a section of the covering unit adapted for covering the rear of the head covering unit. Such a pattern cut has a concave pattern so as to emulate the shape of the front and rear of the head to prohibit the head covering unit from coming off of the head during surgery, and includes a rear panel 20, a front panel 22, a top panel 24, a medial and lateral side panel 26 covering the mid point of the external auditory meatus bilaterally. The seams between the sides containing external aspects so as to contain the head from movement when laying on the posterior side, or the medial or lateral side of the body.

Figure 8:
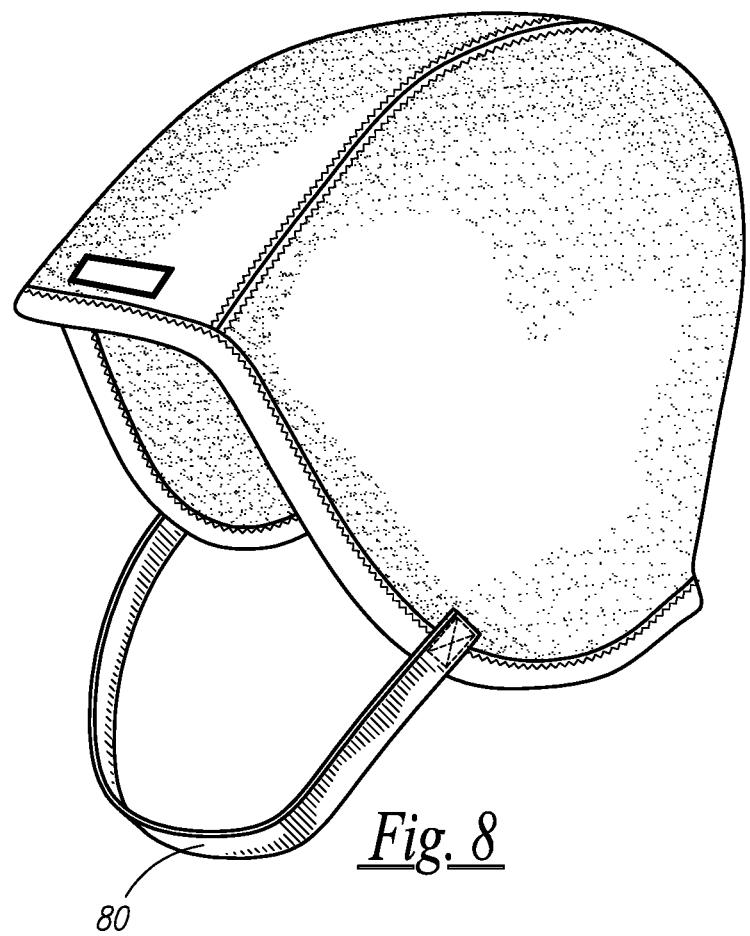

Referring now to FIG. 8, a perspective view of a Surgical Cap for Controlling Patient Body Temperature according to an alternate embodiment of the present invention that includes an additional chinstrap 80 attached to the covering unit 10 across the opening 16 and at the lower edge 18. While the chinstrap 80 is intended to provide additional protection for the prevention of maintaining said head covering on the patient's head during surgery.

2. Operation of the Preferred Embodiment

In operation, the present invention the covering unit 10 is anticipated for use in maintaining the head temperature and core body temperature within euthermic range during or after surgery. The patient's head 70 is covered at the forehead, ears and a base having a back portion along a line where the head and neck meet. The covering unit 10 is closely fitted to the head 70 and maintains a close proximity throughout surgery. The head covering 10 provides further additional insulation at least a portion of a patient's head during surgery. The cap 10 is made such as to grippingly engage below the wearer's external auditory meatus bilaterally and conform closely to the patient's head.

The foregoing descriptions of the specific embodiments of the present invention have been presented for the purposes of illustration and description only. They are not intended to be exhaustive nor are they intended to limit the invention to the precise forms disclosed and, obviously, many modifications and variations are possible in light of the above teaching. The embodiments were chosen and described in order to best explain the principles of the invention and its practical application, to thereby enable others skilled in the art to best utilize the invention and its various embodiments with various modifications as are suited to the particular use contemplated. It is intended that the scope of the invention be defined by the Claims appended hereto and their equivalents. Therefore, the scope of the invention is to be limited only by the following claims.

Having thus described the invention, what is claimed as new and desired and to be secured by Letters Patent is as follows:

1. A surgical cap to maintain a patient's optimal body temperature during a surgical procedure, said surgical cap comprises:
   a shell component, said shell component having an inner surface to closely fit contours of a user's head and over the ears and preventing open air space between said head and said inner surface, said shell component further comprising:
      an outer surface and a lower edge;
      a first side panel;
      a second side panel; and
      a top center panel that forms a front, a center and a rear connected to said first side panel and said second side panel;
   an insulative component lining only a portion of the inner surface along a top center panel about a vertical centerline from a front terminus to a rear and the upper neck region of said insulative component providing greater insulation that about a remainder of the shell component;
   a viewing window formed within said shell component located at a position that corresponds generally to a wearer's forehead region; and
   a gripping structure formed of a medial and a lateral side panel adapted to cover in close proximity a mid point of the external auditory meatus bilaterally, said gripping structure contains the head from shifting and moving when said surgical cap is laid on the posterior, the medial or the lateral side of the body.

2. The surgical cap in claim 1, further comprising in combination a medical temperature trend indicator and wherein said viewing window is adapted to placement over a medical temperature trend indicator placed on the wearer's forehead region.

3. The surgical cap of claim 2, wherein said viewing window comprises:
   a clear rubberized or elastomeric material creating a lense that is flat on the inside and slightly convex on the outside.

4. The surgical cap of claim 3, wherein said shell component has a thickness of between 1 mm and 2 mm and said insulative element comprises material having a thickness greater than 2-mm.

5. The surgical cap of claim 2, wherein said shell component has a thickness of between 1 mm and 2 mm and said insulative element comprises material having a thickness greater than 2-mm.

6. The surgical cap of claim 1, wherein said shell component has a thickness of between 1 mm and 2 mm and said insulative element comprises material having a thickness greater than 2-mm.

7. A surgical cap to maintain a patient's optimal body temperature during a surgical procedure, said surgical cap comprises:
- a shell component having an inner surface, said shell component is adapted to closely fit the contours of a patient's head and over the ears open air space between said head and said inner surface, said shell component further comprises an outer surface that forms an opening circumscribed by a lower edge;
- said shell component forms gripping element to grip a patient's head in a manner that impedes said surgical cap from falling off said patient's head during surgery; and
- a viewing window formed within said shell component located at a position that corresponds to a wearer's forehead region;
- an insulative component, said insulative component lines a portion of said inner surface concomitant with a vertical centerline and having a lateral width of between ¼" to 4".

8. The surgical cap in claim 7, further comprising in combination a medical temperature trend indicator and wherein said viewing window is adapted to placement over a medical temperature trend indicator placed on the wearer's forehead region.

9. The surgical cap of claim 8, wherein said viewing window comprises:
- a clear rubberized or elastomeric material creating a lense that is flat on the inside and slightly convex on the outside.

10. The surgical cap of claim 7, wherein said surgical cap is made from an asymmetric pattern cut from a section of said surgical cap adapted to cover the front of said head and a section of said surgical cap adapted to cover said rear of said head such that said pattern is concave so as to emulate the shape of the front and the rear of said head and to prohibit said surgical cap from falling off.

11. A surgical cap to maintain a patient's optimal body temperature during a surgical procedure, said surgical cap comprises:
- an shell component having an entire area that closely fits a portion of said patient's head and ears and having an inner surface, an outer surface and a lower edge, said inner surface is attached to an insulative element without any voids or pockets formed there between and further comprising:
- a first side panel;
- a second side panel; and
- a top center panel that forms a front, a center and a rear connected to said first side panel and said second side panel;
- said insulative element lining the top center panel comprises material having a thickness greater than 2-mm and having a lateral width concomitant with a vertical centerline and less than the entire shell component;
- a viewing window formed within said shell component located at a frontal, forward facing position that corresponds to a wearer's forehead; and
- a gripping structure formed of a medial and a lateral side panel adapted to cover in close proximity a mid point of the external auditory meatus bilaterally, said gripping element contains the head from shifting and moving when said surgical cap is laid on the posterior, the medial or the lateral side of the body.

12. The surgical cap in claim 11, further comprising in combination a medical temperature trend indicator and wherein said viewing window is adapted to accommodate the use of the medical temperature trend indicator.

13. The surgical cap of claim 11, wherein said viewing window comprises:
- a clear rubberized or elastomeric material creating a lense that is flat on the inside and slightly convex on the outside.

14. The surgical cap of claim 12, wherein said viewing window comprises:
- a clear rubberized or elastomeric material creating a lense that is flat on the inside and slightly convex on the outside.

* * * * *